United States Patent
Fitzgerald et al.

(10) Patent No.: US 6,673,101 B1
(45) Date of Patent: Jan. 6, 2004

(54) APPARATUS AND METHOD FOR DEPLOYING SELF-EXPANDING STENTS

(75) Inventors: Keif M. Fitzgerald, San Jose, CA (US); James C. Shuler, Tracy, CA (US); Patrick P. Wu, Sunnyvale, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/267,338

(22) Filed: Oct. 9, 2002

(51) Int. Cl.[7] .................................................. A61F 2/06
(52) U.S. Cl. ...................... 623/1.11; 606/108; 604/161
(58) Field of Search .................... 604/161; 608/108; 623/1.11, 1.12; 606/108

(56) References Cited

U.S. PATENT DOCUMENTS

| | | | | |
|---|---|---|---|---|
| 4,631,059 A | * | 12/1986 | Wolvek et al. | 604/528 |
| 4,743,265 A | * | 5/1988 | Whitehouse et al. | 604/161 |
| 5,647,857 A | * | 7/1997 | Anderson et al. | 604/264 |
| 5,752,937 A | * | 5/1998 | Otten et al. | 604/161 |
| 6,447,540 B1 | * | 9/2002 | Fontaine et al. | 623/1.12 |

* cited by examiner

Primary Examiner—Corrine McDermott
Assistant Examiner—Thomas J Sweet
(74) Attorney, Agent, or Firm—Fulwider Patton Lee & Utecht, LLP

(57) ABSTRACT

An assembly for delivering a stent to an intraluminal location comprising a catheter having an inner member and an outer member, a stent positioned between the inner member and the outer member at the catheter distal end, and a cutter/slider/deployment mechanism slidable secured to the catheter proximal end. A user may vary the length of the catheter by slidably advancing the cutter/slider/deployment mechanism along the catheter, whereby excess portions of the catheter are cut away. When the desired length is achieved, the user can secure the cutter/slider/deployment mechanism to the catheter to prevent further slidable advancement. The user may also vary the configuration of the catheter handle by adding or removing a removable platform from the handle. Upon stent deployment, the stent is released from the outer member, and the stent will expand as desired.

12 Claims, 5 Drawing Sheets

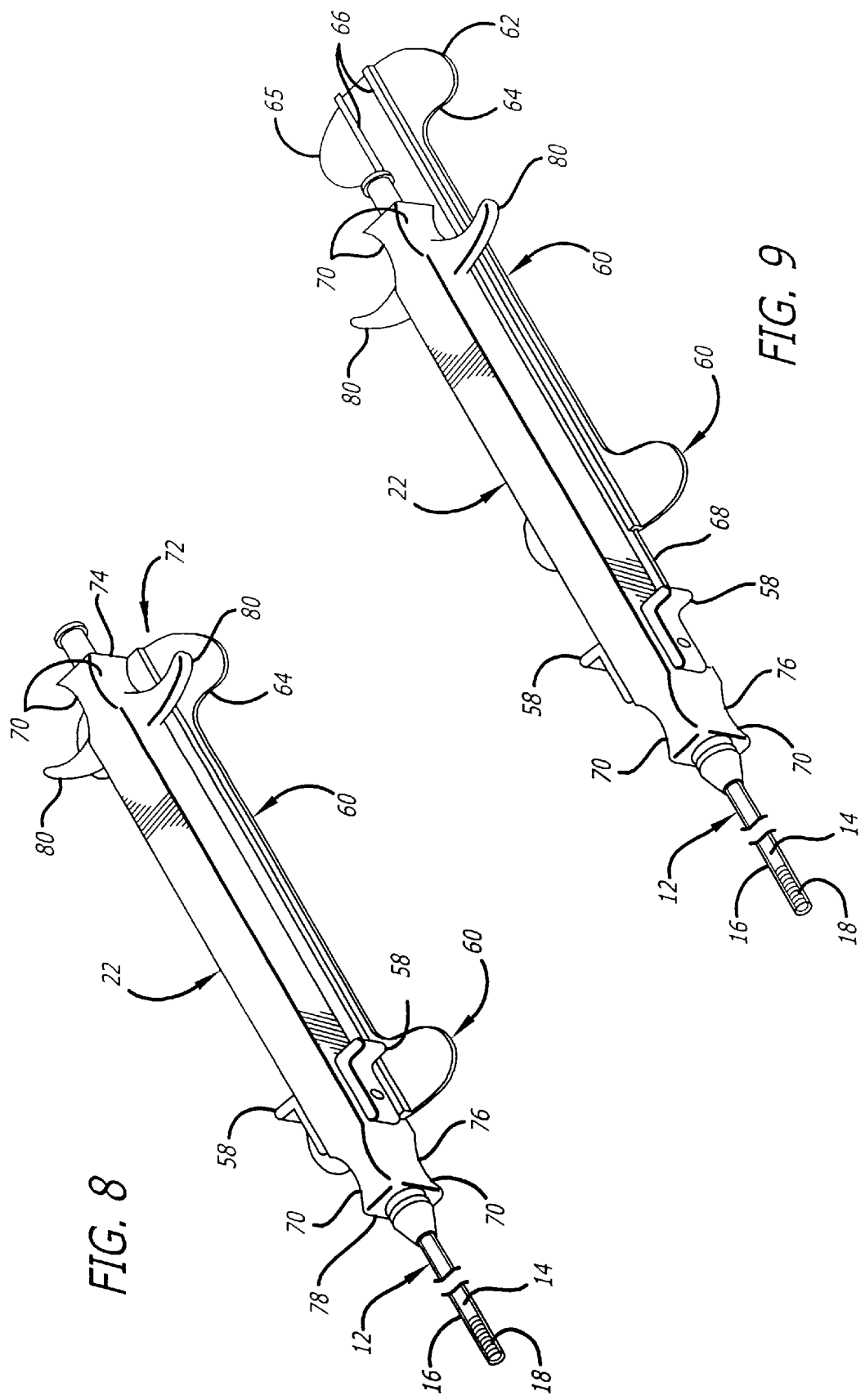

APPARATUS AND METHOD FOR DEPLOYING SELF-EXPANDING STENTS

BACKGROUND OF THE INVENTION

The invention relates generally to a system and method for delivering a stent. More particularly, the invention relates to a stent delivery system (SDS) and method for delivering a self-expanding stent into a body lumen.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having an inflatable balloon on the distal end thereof are introduced through the guiding catheter with the guide wire slidably disposed within an inner lumen of the dilatation catheter. The guide wire is first advanced out of the distal end of the guiding catheter and is then maneuvered into the patient's coronary vasculature containing the lesion to be dilated, and is then advanced beyond the lesion. Thereafter, the dilatation catheter is advanced over the guide wire until the dilatation balloon is located across the lesion. Once in position across the lesion, the balloon of the dilatation catheter is filled with radiopaque liquid at relatively high pressures (e.g., greater than about 4 atmospheres) and is inflated to a predetermined size (which may be the same as the inner diameter of the artery at that location) to radially compress the atherosclerotic plaque of the lesion against the inside of the artery to thereby dilate the lumen of the artery. The balloon is then deflated so that the dilatation catheter can be removed and blood flow resumed through the dilated artery.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon deflation of the balloon, a section of the dissected lining (commonly called a "flap") will collapse into the bloodstream, thereby closing or significantly reducing the blood flow through the vessel. In these instances, emergency bypass surgery is usually required to avoid a myocardial infarct distal to the blockage. Side branches, tortuous vessels, and the more distal arteries have also presented serious difficulties in the PTCA procedure because of the balloon diameter.

Conceivably, the dilatation catheter could be replaced with a perfusion-type dilatation catheter such as described in U.S. Pat. No. 4,790,315 in order to hold the blood vessel open for extended periods. However, some perfusion-type dilatation catheters have relatively large profiles which can make advancement thereof through the blockage difficult, and therefore immediate bypass surgery may be the only means of avoiding an infarct distal to the blockage. Additionally, the inflated balloon of some perfusion-type catheters can block off a branch artery, thus creating ischemic conditions in the side branch distal to the blockage.

In response, one particular endoprosthetic device, known as a stent, has been developed to prevent restenosis and repair damaged vessel walls. Stents are generally tubular-shaped intravascular devices having an expandable or self-expanding structure that is placed within a damaged artery to hold it open. They are particularly suitable for supporting and holding back a dissected arterial lining which could otherwise occlude the fluid passageway there through. The use of stents in non-invasive interventional cardiology has proven to have many advantages, including a net gain in Minimal Lumen Diameter (MLD) of the vessel and reduced restenosis rates.

Stents typically are constructed in one of two general configurations: expandable and self-expanding. Expandable stents require a mechanical force, such as exerted by a balloon disposed within the stent interior, to increase in diameter. Self-expanding stents are generally constructed of shape-memory materials that are biased so that the stent diameter will increase from a reduced diameter maintained by constraining forces to an expanded diameter once the constraining forces are removed, without the action of any external mechanical forces. Some self-expanding stents maintain a reduced diameter at a first temperature range but increase to an expanded diameter at a second temperature range.

Self-expanding stents may be formed in a variety of configurations, and such stents made of coiled wire or springs, braided wire or mesh, and fence-like structures configured in a zig-zag pattern are known in the art.

Delivery systems for self-expanding stents often include a stent circumferentially surrounding the distal end of a delivery catheter. Due to the narrow passageways within the vascular system and particularly the stenotic regions, stents are generally confined in a reduced radius for delivery to the deployment site. Therefore, it can be desirable to keep the profile of the catheter as small as possible to minimize the radius of the stent mounted thereon. For delivery purposes, these stents are typically held in a minimal diameter state by some structure such as a sheath. Upon displacement of the sheath, the stent is exposed to self-expand and contact the vessel wall. Once the stent is deployed, the catheter is removed, leaving the stent implanted at the desired location to keep the vessel walls from closing and allowing time to heal. Another device secures the stent to a catheter without the use of a sheath.

The optimum catheter length for stent delivery can vary depending on the particular procedure, the patient, and the physician. In order to ensure that physicians have a full selection of catheter lengths from which to choose, hospitals often must keep a large inventory of different catheter lengths in stock. Even with such a large stock, however, a physician may find that the hospital does not have the particular length desired. For example, a physician performing a stent deployment procedure in the left common iliac may decide to deliver the catheter contralaterally over the aortic bifurcation, and may desire a catheter having a length of 50 cm for the particular procedure. If the shortest delivery catheter in the hospital's inventory has a length of 80 cm, the physician will often have to make do with the available catheter. The excess catheter length can be awkward for the physician to use, particularly when compared to the optimal length desired by the physician.

During stent delivery procedures, physicians may desire to place the catheter handle on a suitable surface, such as a patient's leg. To meet such needs, some catheter handles have been designed with a platform on one side that is designed to provide stability when the handle is placed on a patient's leg or other suitable surface. However, during some procedures the physician may instead desire to keep the catheter handle in his or her hand, as may be the case where no suitable surface is available on which to place the catheter handle. However, the stability platform that improves the ability of the catheter handle to rest on a surface may feel awkward to a physician who prefers to maintain the catheter handle in his hand.

What has been needed and heretofore unavailable is a stent delivery system with a catheter length and catheter handle configuration that can be selectively varied by the physician, thereby providing the physician with an optimal catheter length and catheter handle configuration while avoiding the need for a hospital to maintain large inventories of catheters with different lengths and handles. The present invention satisfies these needs as well as others.

SUMMARY OF THE INVENTION

The present invention is directed to a device and method for delivering a self-expanding stent using a catheter to deliver and deploy the self-expanding stent, which is particularly suitable for use in coronary arteries to hold vessels open after a balloon angioplasty procedure.

The stent delivery system in accordance with the present invention includes a catheter having an inner member and an outer member. The inner member and outer member are both able to flex in order to traverse tortuous lumens, but the outer member has relatively little or no compliance (that would otherwise permit a self-expanding stent within the outer member to expand radially outwardly.) A stent positioned within the outer member cannot appreciably expand.

In one embodiment of the invention, the self-expanding stent is forced into a constrained position having a low profile or reduced cross section and positioned between the inner member and the outer member of the variable-length catheter.

The stent delivery system includes a mechanism for cutting the catheter to a desired length. The cutting mechanism may cut the outer member, the inner member, or both. In one embodiment of the invention, the cutting mechanism utilizes one or more blades whose cutting edges are configured to engage the outer member along a cutting line running generally parallel to the outer member longitudinal axis. The blade or blades can be advanced longitudinally along the outer member to split apart the outer member.

The stent delivery system further includes a deployment mechanism that serves to hold the inner member secure while the outer member is retracted during stent deployment. The stent delivery system may also include a slider mechanism that permits the cutting mechanism and/or deployment mechanism to be slidably advanced along the catheter.

In one embodiment of the invention, the delivery system includes a combined cutter/slider/deployment mechanism. The cutter/slider/deployment mechanism is slidably secured to a proximal portion of the catheter. The cutter/slider/deployment mechanism is configured so that, as it is slidably advanced along the catheter, excess length of the catheter is cut away from the proximal catheter end. Accordingly, by advancing the cutter/slider/deployment mechanism distally along the catheter, a user can shorten the catheter to a desired length.

In order to allow accurate adjustment of the catheter length, the catheter may include length markings on the catheter itself. A length measurement system may be provided on the catheter packaging.

With the catheter length adjusted to the desired length, the catheter and stent are then introduced into a body lumen and advanced to the treatment site. Once the stent is in the desired position, the outer member can be retracted relative to the stent, so that the stent is no longer restrained by the outer member. The stent can thus expand. The relative movement of the stent and outer member may involve sliding the stent forward along the catheter until it exits the outer member, or withdrawing the outer member along the catheter, or a combination of both. For example, the sliding out of the stent may be accompanied by a simultaneous, equal, and/or and opposite withdrawal of the outer member from the treatment site, so that the stent remains distally motionless with respect to the treatment site. When the stent exits the outer member, the stent can fully deploy into contact with the arterial wall and provide structural support thereto.

In an embodiment where the stent is held fixed relative to the desired treatment location, the outer member slides proximally relative to the desired treatment location, with the stent remaining still with respect to the treatment/deployment location. As the outer member is retracted, the stent expands.

In a further embodiment of the invention, the catheter handle is provided with a removable platform that is configured to improve the stability of the catheter handle when place on a suitable surface, such as on the leg of the patient. The removable platform is releasably secured to the catheter handle, and may be removed in various ways, such as by sliding the removable platform proximally off of the catheter handle.

Other features and advantages of the present invention will become more apparent from the following detailed description of the invention, when taken in conjunction with the accompanying exemplary drawings.

BRIEF DESCRIPTION OF THE DRAWINGS

FIG. 8 is a perspective view of a stent delivery system according to an embodiment of the present invention.

FIG. 9 is a perspective view of the stent delivery system of FIG. 8.

DETAILED DESCRIPTION OF THE PREFERRED EMBODIMENTS

The present invention relates to a stent delivery system in which a self-expanding stent is delivered into a human patient's body lumen, such as a coronary artery, carotid artery, renal artery, or peripheral artery or vein. The invention provides a stent delivery system and method of use in which a stent is implanted in a patient.

Figure 1:
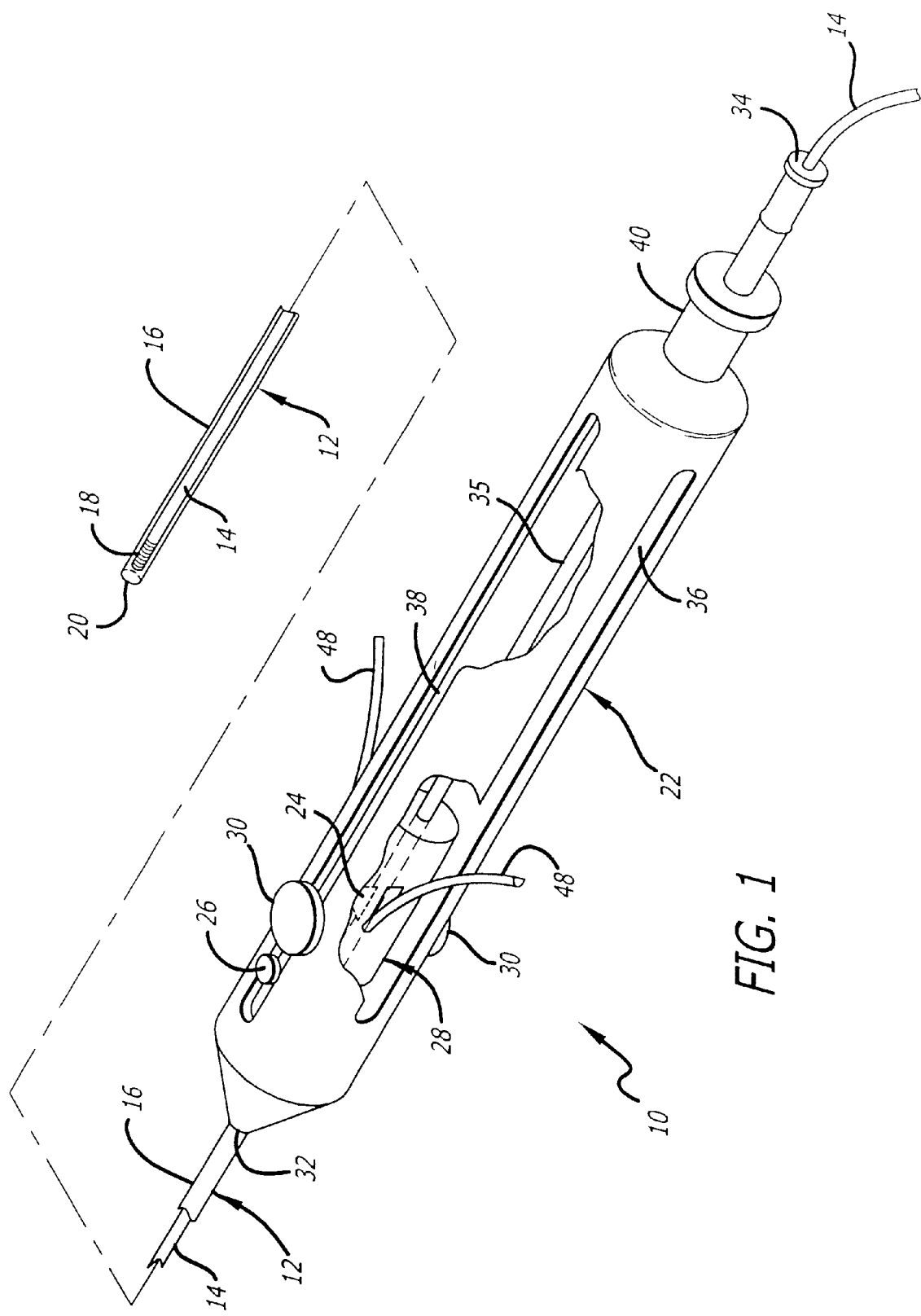
FIG. 1 is a perspective view, in partial cross-section, of a stent delivery system according to an embodiment of the present invention.
Figure 2:
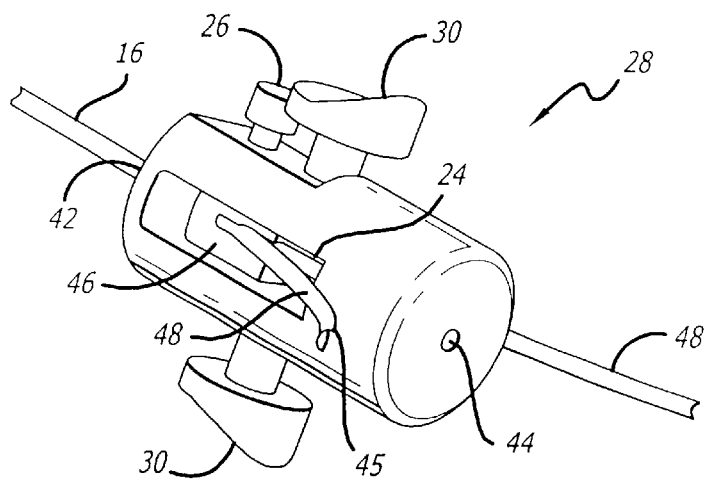
FIG. 2 is a perspective view, in partial cross-section, of a cutter/slider/deployment mechanism according to an embodiment of the present invention.

For purposes of illustration, FIGS. 1 and 2 depict a stent delivery system according to an embodiment of the invention. Generally, stent delivery system 10 includes a generally tubular catheter 12 with a generally tubular inner member 14 and a generally tubular outer member 16, and a stent 18 positioned between the inner member 14 and outer member 16 at the distal end 20 of the catheter 12. A catheter handle 22 is slidably disposed on the catheter 12. A blade 24 or other cutting device slidably disposed on the catheter 12 in a position to engage the outer member 16, and a screw 26 or other gripping mechanism is configured to engage the outer member 16. In the particular embodiment of FIGS. 1 and 2, the blade 24 and screw 26 are incorporated into a combined cutter/slider/deployment mechanism 28 slidably positioned within the catheter handle 22 and on the catheter 12. A catheter handle engaging device is included in the form of one or more slider knobs 30 on the combined cutter/slider/deployment mechanism 28 that releasably engage the catheter handle 22 and thereby control the sliding movement of the combined cutter/slider/deployment mechanism 28 within the catheter handle 22.

In the embodiment of FIG. 1, the catheter handle 22 has a distal opening 32 and a proximal opening 34, and an inner member hypotube 35 passing from the proximal opening 34 to a position proximal of the distal opening 32. The inner member hypotube 35 is configured to permit the inner member 14 to pass therewithin, and also to permit the inner member hypotube 35 to pass within the diameter of the outer member 16.

The catheter handle also has one or more outer member exiting openings 36 and one or more slider openings 38. Note that the outer member exiting openings 36 and slider openings 38 could be combined, so that an opening could serve as both a slider opening and also as an outer member exiting opening. The catheter handle 22 also includes a fastening element 40 configured to releasably secure the catheter inner member 14. In the embodiment of FIG. 1, the fastening element 40 is positioned at the catheter handle proximal opening 34, where it can secure the catheter inner member 14 to prevent unwanted sliding of the catheter inner member 14 through the catheter handle 22.

The combined cutter/slider/deployment mechanism 28, depicted in greater detail in FIG. 2, includes a distal opening 42 and proximal opening 44, as well as an outer member hypotube 45 passing from the proximal opening 44 to a position proximal of the distal opening 42. The outer member hypotube 45 is configured to pass within the outer member 16, and also to permit the inner member hypotube 35 to pass within the outer member hypotube 45. The outer member hypotube 45 provides support for the outer member 16 when the screw 26 engages the outer member 16, and also prevents pressure from the screw 26 in its secured position from causing undue friction between the catheter outer member 16 and the catheter inner member 14 when the catheter outer member 16 is retracted. The combined mechanism 28 also includes one or more outer member openings 46 through which the split portion or portions 48 of the outer member 16 may exit the combined cutter/slider/deployment mechanism 28.

The inner member 14 and outer member 16 enter the catheter handle distal opening 32 and also enter the combined cutter/slider/deployment mechanism distal opening 42. Within the combined cutter/slider/deployment mechanism 28, the catheter outer member 16 is split away from the catheter inner member 14. The outer member split portions 48 are diverted away from the catheter inner member 14, out of the combined cutter/slider/deployment mechanism 28 through the outer member openings 46, and out of the catheter handle through the catheter handle opening 36. The catheter inner member 14 continues through the combined cutter/slider/deployment mechanism 28, exiting through the combined mechanism proximal opening 44, and then passing through the catheter handle proximal opening 34.

One method for adjusting the length of the catheter includes releasing the fastening screw 26, which allows the outer member 16 to slide within the combined mechanism 28. The inner member fastening device 40 is also released, permitting the inner member 14 to slide within the catheter handle 22. The user can then grip the outer member 16 at a position distal of the catheter handle 22. With the slider knobs 30 left in a locked position to preventing the combined mechanism 28 from sliding with respect to the catheter handle 22, the user advances the catheter handle 22 distally along the catheter 12. As the catheter handle 22 is advanced, the combined mechanism 28 is also advanced. The blades 24 split apart the outer member 16, with the split portions 48 being peeled away from the inner member 14 and forced out of the catheter handle. Note that although the embodiment of FIG. 2 has two blades 24 that split the outer member 16 along two generally parallel cutting lines extending along the outer member 16, other configurations are also within the scope of the invention. For example, a single blade could split the outer member along a single cutting line, thus creating a single split portion out of the outer member that could be peeled away from the inner member. Three or more blades could also be used, and the blades could follow various cutting lines.

When portion of the catheter 12 distal of the catheter handle 22 is of a desired length, the user stops advancing the catheter handle 22. The fastening screw 26 is secured to prevent the catheter outer member 16 from sliding with respect to the combined mechanism 28, and the inner member fastening element 40 is secured to the inner member 14. Accordingly, the outer member 16 is now secured to the combined mechanism 28, but the inner member 14 is secured to the catheter handle 22.

Depending on how far the catheter handle has been advanced, there may be a substantial length of the outer member split portions 48 and the portion of the inner member 14 that is proximal of the catheter handle 22. These excess portions could be a distraction to the user during a stent deployment procedure. The outer member split portions 48 can be removed with an external cutting device, such as a pair of scissors. Similarly, the portion of the inner member 14 that is proximal of the catheter handle 22 can also be cut away with an external cutting device. Alternatively, the catheter handle 22 could be equipped with one or more cutting devices configured to trim off the excess portions of the outer member and inner member. In another embodiment, the catheter handle 22 could be configured to store the excess portions of the outer member and/or inner member.

Figure 3:
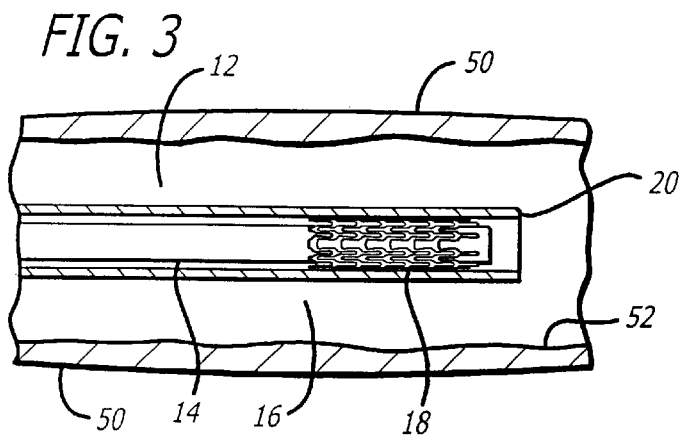
FIG. 3 is a side view, in cross-section, of the stent delivery system of FIGS. 1 and 2 used to deploy a stent in a vessel.
Figure 4:
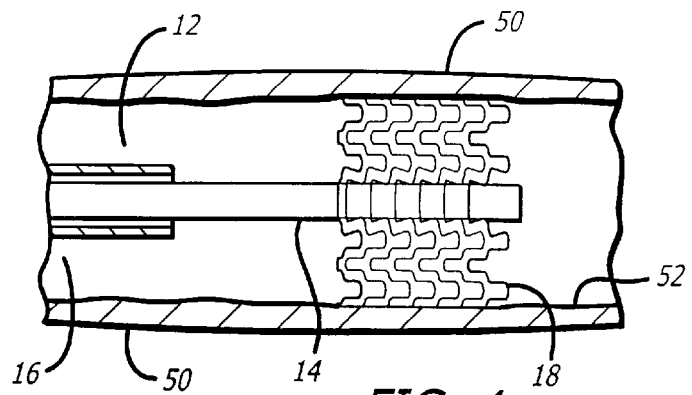
FIG. 4 is a side view, in cross-section, of the stent delivery system of FIGS. 1 and 2 used to deploy a stent in a vessel.

With the catheter 12 trimmed to the desired length, the user can advance the stent deployment device into a desired body lumen of the patient, such as a part of the cardiovascular system of the patient, until the stent is at the desired location for treatment. By way of example, FIG. 3 depicts the catheter 12 of FIGS. 1 and 2 with the catheter distal end 20 advanced within an artery 50 with the stent 18 positioned at a desired treatment location 52. To deploy the stent, the user depresses the slider knobs 30, thereby slidably releasing the combined mechanism 28 from the catheter handle 22. With the catheter handle 22 held still so that the stent 18 remains at the desired treatment location 52, the user slides the combined mechanism 28 proximally within the catheter handle 22, thereby sliding the catheter outer member 16 proximally over the catheter inner member 14. At the catheter distal end 20, the proximal withdrawal of the catheter outer member 16 releases the stent 18, and the stent 18 is deployed at the desired location 52, as depicted in FIG. 4.

Figure 5:
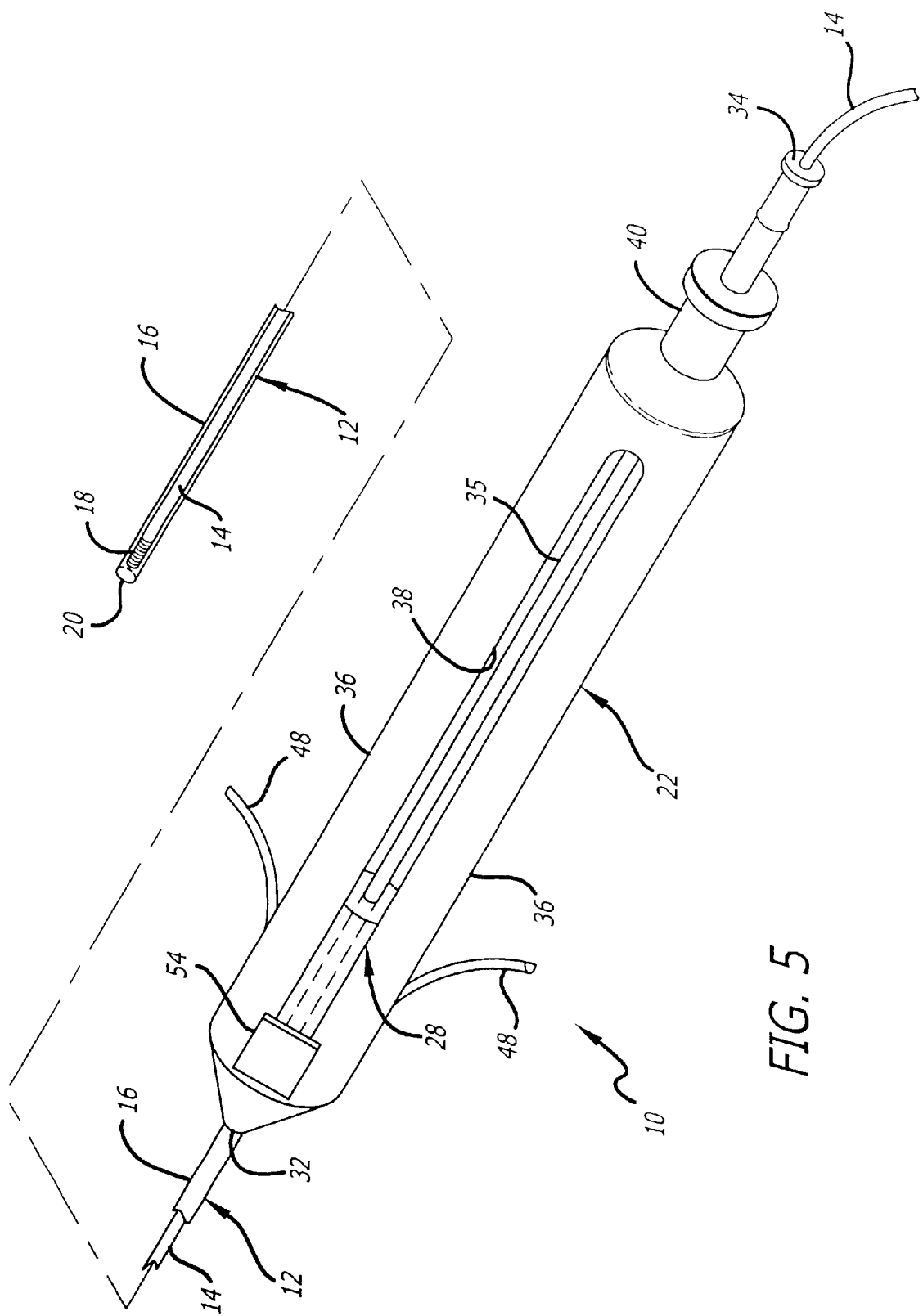
FIG. 5 is a perspective view, in partial cross-section, of a stent delivery system according to an embodiment of the present invention.
Figure 6:
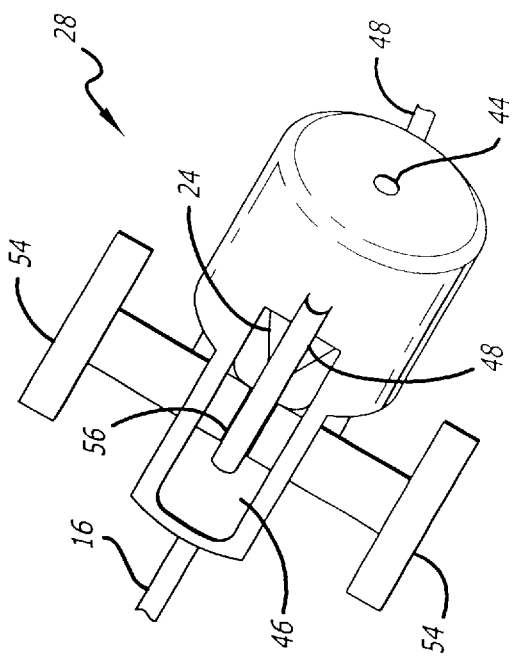
FIG. 6 is a perspective view, in partial cross-section, of a cutter/slider/deployment mechanism according to an embodiment of the present invention.

FIGS. 5 and 6 depict a further embodiment of the invention. Instead of the screw 26 and slider knob 30 of FIGS. 1 and 2, the combined mechanism uses one or more combined slider/gripper knobs 54. In the "out" position, the combined slider/gripper knobs 54 engage the slider knob openings 38 to prevent the combined mechanism 28 from sliding within the catheter handle 22, but do not engage the catheter outer member 16. When depressed by a user, the grippers 56 on the combined slider/gripper knobs 54 engage the catheter outer member 16, while the slider/gripper knobs 54 also slidably release the slider knob openings 38 so that the combined mechanism 28 can slide within the catheter handle 22.

One method for using the embodiment of FIGS. 5 and 6 for adjusting the length of the catheter includes releasing the inner member fastening device 40, permitting the inner member 14 to slide within the catheter handle 22. The user can then grip the outer member 16 at a position distal of the catheter handle 22. With the combined slider/gripper knobs 54 left in the "out" position, whereby the combined mechanism 28 is prevented from sliding with respect to the catheter handle 22, the user advances the catheter handle 22 distally along the catheter 12. The blades 24 split apart the outer member 16, with the split portions 48 being forced out of the catheter handle. When the portion of the catheter 12 distal of the catheter handle 22 is of a desired length, the user stops advancing the catheter handle 22. The inner member fastening element 40 is secured to the inner member 14.

To deploy the stent, the user depresses the combined slider/gripper knobs 54, thereby slidably releasing the combined mechanism 28 from the catheter handle 22 while simultaneously engaging the gripper 56 to securing the combined mechanism 28 to the catheter outer member 16. With the catheter handle 22 held still so that the stent 18 remains at the desired treatment location, the user slides the combined mechanism 28 proximally within the catheter handle 22, thereby sliding the catheter outer member 16 proximally over the catheter inner member 14. At the catheter distal end 20, the proximal withdrawal of the catheter outer member 16 releases the stent 18, and the stent 18 is deployed into the desired location.

Figure 7:
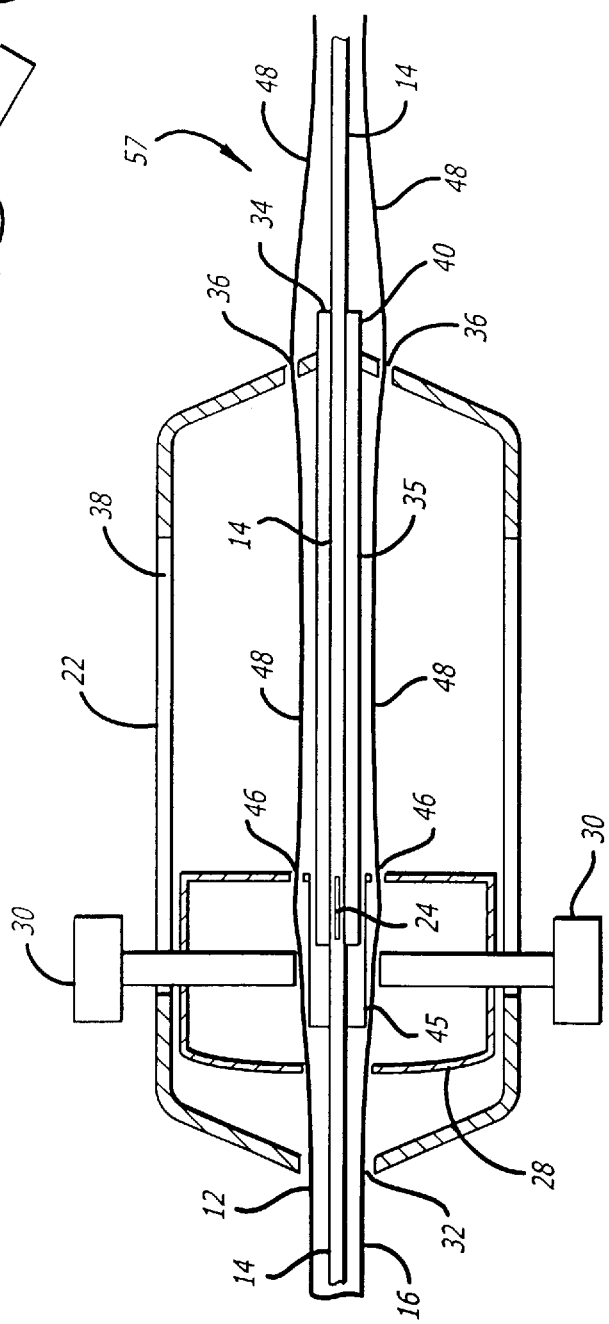
FIG. 7 is a side view, in partial cross-section, of a stent delivery system according to an embodiment of the present invention.

FIG. 7 depicts a further embodiment of the invention. Instead of having the outer member split portions 48 exit through openings in the sides of the catheter handle 22, the exit openings 36 through which the outer member split portions 48 exit the catheter handle 22 are positioned adjacent to the proximal opening 34 through which the inner member 14 exits the catheter handle 22. The exit openings 46 in the combined mechanism 28 are configured to permit the split portions 48 to pass generally adjacent to the central axis of the catheter handle 22. Accordingly, after the outer member 16 is split by the cutting blades 24, the split portions 48 are directed generally along the inner hypotube 35 and inner member 14, and upon exiting from the catheter handle 22 run parallel and adjacent to the inner member 14. A user can easily and simultaneously grip the outer member split portions 48 and the inner member 14 at a position 57 proximal of the catheter handle 22.

One method for adjusting the length of the catheter using the embodiment of FIG. 7 includes releasing the fastening screw or other securing device (if present) to allow the outer member 16 to slide within the combined mechanism 28. The inner member fastening device 40 is also released, permitting the inner member 14 to slide within the catheter handle 22. The user can then grips the outer member split portions 48 and inner member 14 at a position proximal of the catheter handle 22. With the slider knobs 30 left in a locked position to preventing the combined mechanism 28 from sliding with respect to the catheter handle 22, the user advances the catheter handle 22 distally along the catheter 12. Advancing the catheter handle 22 may involve pulling the catheter 12 through the catheter handle 22, which is accomplished by the user gripping and pulling on the outer member split portions 48 and/or the inner member 14 proximal of the handle 22.

As the catheter handle 22 is advanced, the combined mechanism 28 is also advanced. The blades 24 split apart the outer member 16, with the split portions 48 passing generally along the inner member 14 and out through exit openings 36 of the catheter handle 22.

When the portion of the catheter 12 distal of the catheter handle 22 is of a desired length, the user stops advancing the catheter handle 22. The fastening screw (if present) is secured to prevent the catheter outer member 16 from sliding with respect to the combined mechanism 28, and the inner member fastening element 40 is secured to the inner member 14. Thus, the outer member 16 is now secured to the combined mechanism 28, with the inner member 14 secured to the catheter handle 22.

FIGS. 8 and 9 depict a further embodiment of the invention. The embodiment depicted includes a catheter 12 having an inner member 14 and outer member 16 with a stent 18 positioned between the inner member 14 and outer member 16. The embodiment also includes a catheter handle 22 with a slidable deployment gripper 58, such as the slider knob from the embodiment of FIGS. 1 and 2, which is secured directly or indirectly to the catheter outer member 16. When the deployment gripper 58 is slid proximally along the catheter handle 22, the outer member 16 is retracted proximally to release/deploy the stent 18.

The catheter handle 22 of FIGS. 8 and 9 includes a removable platform 60. The removable platform 60 is configured to increase the stability of the catheter handle 22 when placed on a surface, such as a patient's leg. The particular removable platform 60 depicted includes protruding stabilizers 62 that extend outwardly from the removable platform 60 and also extend beyond the width of the main body of the catheter handle 22, thus preventing the catheter handle 22 from tipping sideways on the surface. The lower surface 64 of the removable platform 60 may be slightly curved to conform to a desired surface, such as a patient's leg. The removable platform 60 depicted has an upper surface 65 having grooves 66 which are configured to receive tracks 68 running along the edge of the catheter handle 22. The removable platform 60 can be slidably removed from the catheter handle 22, as depicted in FIG. 10. The removable platform 60 may be held in place on the catheter handle 22 by friction between the grooves 66 and tracks 68. A locking mechanism may be provided to prevent the removable platform 60 from accidentally sliding off of the catheter handle 22. Other methods of securing and removing the removable platform are also within the scope of the invention, such as providing a removable platform that can be snapped off of the catheter handle.

The catheter handle of FIGS. 8 and 9 also includes indentations 70 configured to receive the user's fingers. In the embodiment depicted, the indentations 70 are positioned in a first set 72 adjacent the proximal end 74 and in a second set 76 adjacent the distal end 78 of the catheter handle 22, so that a user may select to use either set of indentations. Also adjacent to the proximal end 74 of the catheter handle 22 is a pair of extensions 80 configured to be engaged by a user's fingers.

The dimension and materials used to form the catheter can vary, depending on the particular application. For example, dimensions for peripheral use will vary from coronary applications, as is known in the art. The materials of construction of the catheter may be selected, for example, from those used in conventional stent delivery catheters. Polymers, including non-compliant and compliant polymers, may be used to form the catheter. The specific dimensions and materials of construction of the catheter set forth herein are provided as examples, and substitutes are readily contemplated which do not depart from the invention.

The stents as described herein may be formed from any number of materials, including materials displaying shape memory characteristics such as metals, metal alloys, and polymeric materials that can be constrained in a reduced delivery profile and upon release assume an enlarged deployed diameter. The stents may formed from metal alloys such as stainless steel, tantalum, or nickel-titanium (NiTi).

Although the invention has been depicted in conjunction with a catheter for deploying self-expanding stents, the invention is applicable to various catheter designs. For example, the removable platform could be used with inflatable balloon catheters that are often used to deliver and deploy balloon-expandable stents.

While the present invention has been described herein in terms of delivering a stent to a desired location within a patient's blood vessel, the delivery system can be employed to deliver stents to locations within other body lumens such as urethra or Fallopian tubes so that the stents can be expanded to maintain the patency of these body lumens. It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed:

1. A stent delivery assembly, comprising:
   a generally tubular catheter having an inner member and an outer member;
   a stent disposed between the outer member and the inner member;
   a catheter handle; and
   a cutting mechanism slidably secured to the catheter handle, the cutting mechanism positioned in contact with the catheter outer member.

2. The assembly of claim 1, wherein the cutting mechanism comprises a blade.

3. The assembly of claim 1, wherein the cutting mechanism is slidably disposed on the catheter outer member.

4. The assembly of claim 3,
   wherein the catheter handle is slidably disposed on the catheter.

5. The assembly of claim 4, further comprising:
   a slider mechanism slidably secured to the outer member, the slider mechanism comprising a securing mechanism configured to releasably secure the slider mechanism to the catheter outer member,
   wherein the cutting mechanism is secured to the slider mechanism.

6. A stent delivery assembly, comprising:
   a generally tubular catheter having an inner member and an outer member;
   a stent disposed between the outer member and the inner member;
   a cutting mechanism slidably disposed on the catheter, the cutting mechanism positioned in contact with the catheter outer member;
   wherein the cutting mechanism is slidably disposed on the catheter outer member;
   a catheter handle slidably disposed on the catheter;
   a slider mechanism slidably disposed on the outer member, the slider mechanism comprising a securing mechanism configured to releasably secure the slider mechanism to the catheter outer member;
   wherein the cutting mechanism is secured to the slider mechanism;
   wherein the slider mechanism is slidably positioned within the catheter handle, whereby the slider mechanism may be slid with respect to the catheter handle.

7. The assembly of claim 6, wherein the slider mechanism comprises a catheter handle engaging device that releasably engages the catheter handle to prevent sliding of the slider mechanism with respect to the catheter handle.

8. The assembly of claim 6, wherein the catheter handle comprises an outer member locking mechanism for fixedly securing the handle to the catheter outer member.

9. The assembly of claim 6, wherein the catheter handle comprises an inner member locking mechanism for fixedly securing the handle to the catheter inner member.

10. A catheter assembly comprising:
    a generally tubular catheter having an outer member;
    a catheter handle slidably disposed on the catheter outer member and including structure that secures the handle to the outer member;
    a cutting mechanism slidably disposed on the catheter outer member and slidably secured to the catheter handle.

11. The catheter assembly of claim 10, wherein the cutting mechanism is positioned within the catheter handle.

12. The catheter assembly of claim 10, wherein the cutting mechanism comprises a blade engaging the catheter outer member.

* * * * *